US006387889B1

(12) United States Patent
Endo et al.

(10) Patent No.: US 6,387,889 B1
(45) Date of Patent: May 14, 2002

(54) MEDICINAL COMPOSITIONS FOR TREATING EYE DISEASES

(75) Inventors: Kazuki Endo, Narita; Toichi Abiru, Sawara; Tomokazu Hosokawa, Sagamihara; Miwa Misawa, Tokyo; Takashi Konno, Fukushima, all of (JP)

(73) Assignees: Yamasa Corporation, Choshi; Toa Eiyo Ltd., Tokyo, both of (JP)

( * ) Notice: Subject to any disclaimer, the term of this patent is extended or adjusted under 35 U.S.C. 154(b) by 0 days.

(21) Appl. No.: 09/786,126

(22) PCT Filed: Aug. 31, 1999

(86) PCT No.: PCT/JP99/04709

§ 371 Date: Mar. 1, 2001

§ 102(e) Date: Mar. 1, 2001

(87) PCT Pub. No.: WO00/12098

PCT Pub. Date: Mar. 9, 2000

(30) Foreign Application Priority Data

Sep. 1, 1998 (JP) .......................................... 10-246826

(51) Int. Cl.[7] .............................................. A61K 31/70
(52) U.S. Cl. .......................... 514/46; 514/912; 514/913
(58) Field of Search ........................................... 514/46

(56) References Cited

U.S. PATENT DOCUMENTS 5,039,797 A    8/1991  Clack et al. ................... 536/49

5,593,975 A  *  1/1997  Cristalli

FOREIGN PATENT DOCUMENTS

JP        1-146895        6/1989
WO        WO93/22328   *  11/1993

OTHER PUBLICATIONS

T. Abiru, et al., European Journal of Pharmacology, vol. 196, No. 1, pp. 69–76, "The Antihypertensive Effect of 2–Alkynyladenosines and Their Selective Affinity for Adenosine $A_2$ Receptors", 1991.

C. E. Crosson, The Journal of Pharmacology and Experimental Therapeutics, vol. 273, No. 1, pp. 320–326, "Adenosine Receptor Activation Modulates Intraocular Pressure in Rabbits", 1995.

* cited by examiner

Primary Examiner—Minna Moezie
Assistant Examiner—Mojdeh Bahar
(74) Attorney, Agent, or Firm—Oblon, Spivak, McClelland, Maier & Neustadt, P.C.

(57) ABSTRACT

Medicinal compositions for treating eye diseases which contain as the active ingredient 2-alkynyladenosine derivatives having an acetylene union at the 2-position of adenine base. Having a long-lasting and remarkable effect of lowering ocular tension, these compositions are useful as remedies for eye diseases accompanying increased ocular tension or optic nerve failures, such as glaucoma and hypertonia oculi.

18 Claims, 2 Drawing Sheets

MEDICINAL COMPOSITIONS FOR TREATING EYE DISEASES

DESCRIPTION

This application is a 371 of PCT/JP99/04709 filed Aug. 31, 1999.

1. Technical Field

The present invention relates to medicinal compositions for treating eye diseases, which are useful for treating eye diseases accompanying increased ocular tension and/or optic neuropathy, such as glaucoma and hypertonia oculi.

2. Background Art

Glaucoma and hypertonia oculi are eye diseases which can occur in all mammals (e.g., primates), and are also intractable eye diseases which are characterized by optic neuropathy attributed to an increase in intraocular pressure (increase in ocular tension) or autoregulation dysfunction of aqueous humor and intraocular blood circulation. Symptoms of glaucoma include eye pain, headaches, rainbow symptoms, nephelopsia, decrease in visual acuity, eye congestion, nausea, vomiting, bradycardia, sweating, and visual field anomaly. In some cases, subjective symptoms of glaucoma do not arise until the disease is in its advanced stages.

Increase in ocular tension is caused by imbalance between the secretion rate of aqueous humor, which is secreted from the ciliary epithelium to the posterior chamber, and the elimination rate of aqueous humor, which is eliminated from the anterior chamber mainly through the Schlemm's canal. In many cases, this imbalance is considered to be caused by increase in the flow resistance of aqueous humor which does not circulate at the gonio-portion.

Conventionally, glaucoma had been considered to be caused by mechanical optic neuropathy due to increase in ocular tension. However, according to a recent convincing theory, glaucoma is considered to be caused by secretion of aqueous humor in the ciliary body; elimination of aqueous humor from the gonio-trabecule to the Schlemm's canal; or neurovascular disturbance due to autoregulation dysfunction of blood circulation at the optic papilla. Therefore, although increase in ocular tension is the major dysfunction factor, all factors related to embrittlement of the optic papilla or hematogenic disorder at the optic papilla are considered risk factors.

Recently, normal ocular tension glaucoma has become widely known, and ocular tension is not an absolute factor in the diagnosis of glaucoma. However, regardless of whether ocular tension is high or normal, controlling of ocular tension, which is the major risk factor for glaucoma, is most important for the treatment of glaucoma.

Glaucoma is a significant disease, and the number of patients suffering from glaucoma has been increasing year by year in developed countries experiencing aging of their populations. In such societies, the need for glaucoma remedies is expected to increase in the future.

At the present time, β-blockers, prostaglandin derivatives, and carbonate dehydrogenase inhibitors are known as glaucoma remedies. These drugs are known to exhibit the effect of lowering ocular tension through controlling secretion or elimination of aqueous humor.

Recently, an adenosine derivative which is an adenosine A2 receptor agonist: CGS-21680 [2-((4-(2-carboxyethyl) phenylethyl)amino)adenosine-5'-N-ethyluronamide] has been reported to have the effect of lowering ocular tension (J. Pharmacol. Exp. Ther. 273, 320–326 (1995)). However, this effect is not satisfactory, and there has been much demand for the development of more effective drugs.

DISCLOSURE OF THE INVENTION

In general, since the affinity to an adenosine receptor correlates with the hypotensive effect, an adenosine derivative is considered to exhibit the effect of lowering blood pressure through vasodilation in connection with an adenosine receptor (J. Pharmacol. Exp. Ther. 247, 882–888, 1988 and Eur. J. Pharmacol. 196, 69–76, 1991). For example, CGS-21680 has been reported to have affinity to an adenosine A2 receptor, and to exhibit the effect of lowering blood pressure. Also, 2-octynyladenosine has been reported to have affinity to an adenosine A2 receptor, to exhibit the effect of lowering blood pressure, and to be useful as a hypotensive drug, a preventive drug or a remedy for ischemic heart or brain diseases, and a preventive drug or a remedy for arteriosclerosis (Japanese Patent Publication (kokoku) Nos. 1-33477 and 2-17526, Japanese Patent No. 2774169, and Japanese Patent Application Laid-Open (kokai) No. 3-287537).

In view of the foregoing, the present inventors have anticipated that, similar to CGS-21680, other adenosine derivatives having affinity to an adenosine receptor may exhibit the effect of lowering ocular tension, although such derivatives have not yet been researched on the treatment of eye diseases. The present inventors have performed extensive studies on the relation between the affinity to an adenosine receptor and the effect of lowering ocular tension. Consequently, they have found that, surprisingly, the affinity of the adenosine derivatives to an adenosine receptor is not proportional to the effect of lowering ocular tension; that differences in the physical properties of compounds greatly affect the distribution of absorption; and that affinity to an adenosine receptor cannot serve as the basis for screening compounds with regard to whether or not they have the effect of lowering ocular tension. Therefore, the present inventors have carried out random screening of a variety of adenosine derivatives on the basis of the effect of lowering ocular tension. As a result, they have found that 2-alkynyladenosine derivatives having an acetylene union at the 2-position of the adenine base exhibit an excellent and long-lasting effect of lowering ocular tension, as compared with CGS-21680; and that such derivatives are useful as remedies for eye diseases such as glaucoma and hypertonia oculi. The present invention has been accomplished on the basis of these findings.

Accordingly, the present invention provides a medicinal composition for treating eye diseases, which comprises, as an active ingredient, a 2-alkynyladenosine derivative having an acetylene union at the 2-position of the adenine base.

The present invention also provides use of a 2-alkynyladenosine derivative having an acetylene union at the 2-position of the adenine base for the production of a medicinal composition for treating eye diseases.

The present invention also provides a method for the treatment of eye diseases, which comprises administration of a 2-alkynyladenosine derivative having an acetylene union at the 2-position of the adenine base.

BEST MODES FOR CARRYING OUT THE INVENTION

Figure 1:
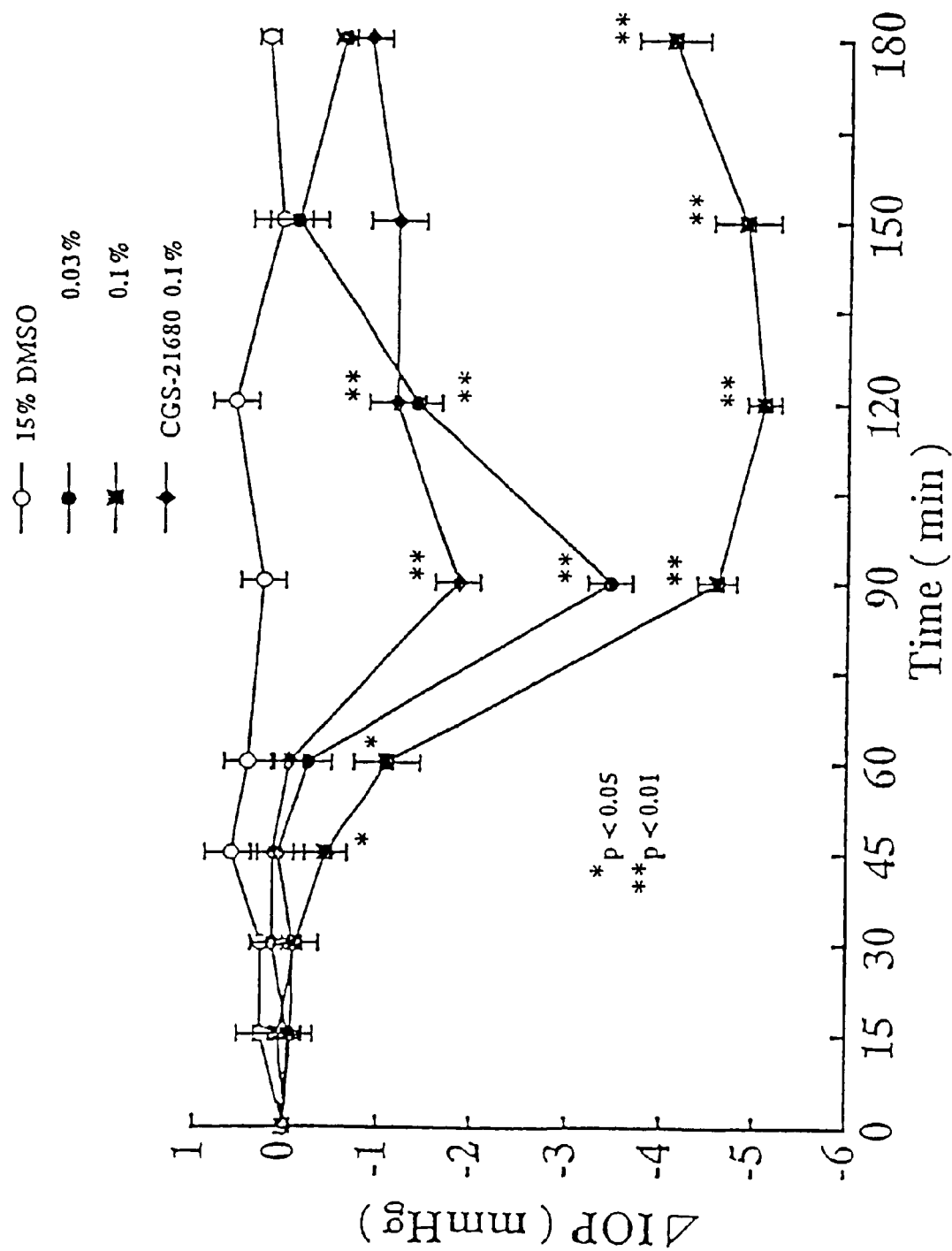
FIG. 1 shows the effect of 2-(1-octynyl)adenosine (●, ■) and CGS-21680 (♦) against ocular tension in rabbits when administered to the rabbits. The y axis represents change in ocular tension (ΔIOP), and the x axis represents time (minutes) elapsed after administration.

The 2-alkynyladenosine derivative used in the medicinal compositions for treating eye diseases of the present invention is not particularly limited, so long as the derivative has an acetylene union at the 2-position of the adenine base.

Specific examples of the 2-alkynyladenosine derivative include the compounds represented by the following formula

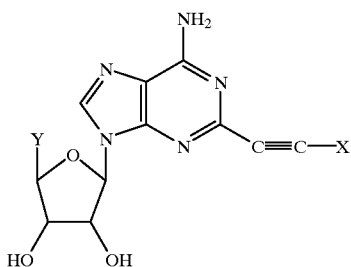

(1)

[wherein X represents a hydrocarbon group or an acyl group which may have a substituent; and Y represents a substituted methyl group, a carbamoyl group which may have a substituent, or a carboxyl group which may be esterified.]

In formula (1), a hydrocarbon group represented by X is preferably a C1–C20 hydrocarbon group, and may be a saturated hydrocarbon group or an unsaturated hydrocarbon group. Specific examples include an alkyl group, an alkenyl group, an alkynyl group, a cycloalkyl group, an aryl group, an aralkyl group, and a cycloalkyl-substituted alkyl group.

Examples of alkyl groups, alkenyl groups, and alkynyl groups include C1–C20 linear or branched alkyl groups, alkenyl groups, and alkynyl groups. Specific examples of alkyl groups include linear alkyl groups such as a methyl group, an ethyl group, an n-propyl group, an n-butyl group, an n-pentyl group, an n-hexyl group, an n-octyl group, an n-decyl group, an n-dodecyl group, and an n-tetradecyl group; and branched alkyl groups such as an isopropyl group, an isobutyl group, a t-butyl group, and a 2-ethylhexyl group. Specific examples of alkenyl groups include a vinyl group, a propenyl group, and an allyl group. Specific examples of alkynyl groups include an ethynyl group, a propynyl group, and a butynyl group. Examples of cycloalkyl groups include C3–C10 cycloalkyl groups. Of these, a C3–C8 cycloalkyl group, for example, a cyclopropyl group, a cyclopentyl group, or a cyclohexyl group is preferable. Examples of aryl groups include C6–C14 aryl groups, such as a phenyl group, a tolyl group, and a naphthyl group. Examples of aralkyl groups include C7–C14 aralkyl groups, such as a benzyl group and a phenethyl group. Examples of cycloalkyl-substituted alkyl groups include $C_3$–$C_8$ cycloalkyl-substituted $C_1$–$C_{10}$ alkyl groups, such as a cyclopropylmethyl group, a cyclopentylmethyl group, a cyclohexylmethyl group, a cyclopropylethyl group, a cyclopentylethyl group, a cyclohexylethyl group, a cyclopropylpropyl group, a cyclopentylpropyl group, and a cyclohexylpropyl group.

Examples of substituents on the hydrocarbon group include a hydroxyl group, an azido group, a cyano group, an oxygen-substituted hydrocarbon (hydrocarbon-oxy) group, a carboxyl group which may be esterified, and groups represented by the following formulas (A) through (C):

—NHCOR$^1$ (A)

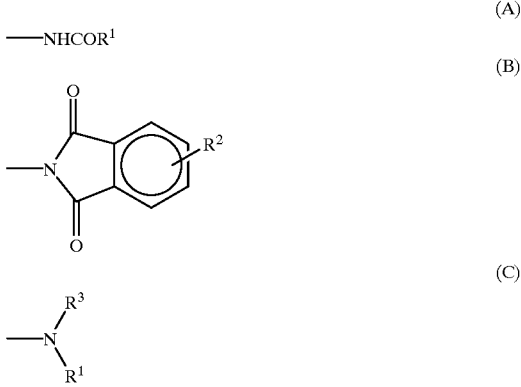

(B)

$$-N\begin{matrix}R^3\\R^1\end{matrix}$$ (C)

(wherein $R^1$ represents an alkyl group, an aryl group, an aralkyl group, or a halogenated alkyl group; $R^2$ represents a hydrogen atom, an alkyl group, an alkoxy group, or a halogen atom; and each of $R^3$ and $R^4$ which are identical to or different from each other, represents a hydrogen atom, an alkyl group, a cycloalkyl group, or an aryl group.)

Examples of oxygen-substituted hydrocarbon (hydrocarbon-oxy) groups include an alkoxy group, a cycloalkyloxy group, and an aryloxy group. A preferred alkoxy group is a C1–C10 alkoxy group; a preferred cycloalkyloxy group is a C3–C8 cycloalkyloxy group; and a preferred aryloxy group is a C6–C14 aryloxy group. Examples of aryloxy groups include a phenoxy group, and a substituted phenoxy group having a substituent such as a halogen atom, an alkyl group, or an alkoxy group.

Examples of carboxyl groups which may be esterified include a carboxyl group, an alkoxycarbonyl group, a cycloalkyloxycarbonyl group, and an aryloxycarbonyl group. Alkoxy, cycloalkyloxy, and aryloxy groups are similar to those described above.

Examples of alkyl groups represented by each of $R^1$, $R^2$, $R^3$, and $R^4$ include C1–C10 alkyl groups. Examples of aryl groups include C6–C14 aryl groups, such as a phenyl group, a tolyl group, a naphthyl group, a halogenated phenyl group, and an alkoxyphenyl group. Examples of aralkyl groups include C7–C14 aralkyl groups, such as phenyl-substituted $C_1$–$C_6$ alkyl groups. Examples of halogenated alkyl groups include $C_1$–$C_{10}$ alkyl groups substituted by one to three halogen atoms, such as a fluorine atom, a chlorine atom, a bromine atom, and an iodine atom. Examples of alkoxy groups include C1–C10 alkoxy groups. Examples of cycloalkyl groups include C3–C8 cycloalkyl groups. Examples of halogen atoms include a fluorine atom , a chlorine atom, a bromine atom, and an iodine atom.

Examples of acyl groups represented by X include a formyl group, an alkanoyl group, a cycloalkylcarbonyl group, and an aroyl group. A preferred alkanoyl group is a C2–C11 l linear or branched alkanoyl group; a preferred cycloalkylcarbonyl group is a C4–C9 cycloalkylcarbonyl group; and a preferred aroyl group is a C7–C15 aroyl group, such as a benzoyl group, a naphthoyl group, or a benzoyl group substituted by a halogen atom, an alkyl group, or an alkoxy group.

Examples of substituents on a methyl group represented by Y include a hydroxyl group, an azido group, and a group represented by the following formula (D):

—NHR$^5$ (D)

(wherein $R^5$ represents a hydrogen atom, a group

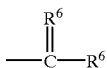

or a group —$SO_2$—$R^8$; $R^6$ represents an oxygen atom or a sulfur atom; $R^7$ represents a hydrogen atom, an alkyl group, an amino group, or an alkylamino group; and $R^8$ represents an alkyl group or an aryl group.)

An alkyl group and an aryl group represented by $R^7$ and $R^8$ in formula (D) are the same as those represented by the aforementioned $R^1$ through $R^4$. A preferred alkylamino group is a C1–C10 alkylamino group.

Examples of carbamoyl groups which may have a substituent, represented by Y, include a group represented by the following formula (E):

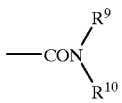

(E)

(wherein each of $R^9$ and $R^{10}$, which are identical to or different from each other, represents a hydrogen atom, an alkyl group, or a cycloalkyl group.)

An alkyl group and a cycloalkyl group represented in formula (E) are the same as those represented by the aforementioned $R^1$ through $R^4$.

Examples of carboxyl groups which may be esterified represented by Y include, as described above, a carboxyl group, an alkoxycarbonyl group, a cycloalkyloxycarbonyl group, and an aryloxycarbonyl group.

Exemplary compounds of the 2-alkynyladenosine derivatives represented by formula (1) are described below.
(1) X=hydrocarbon, Y=—$CH_2OH$
2-(1-Pentynyl)adenosine
2-(1-Hexynyl)adenosine (Compound 1)
2-(1-Heptynyl)adenosine
2-(1-Octynyl)adenosine (Compound 2)
2-(1-Hexadecynyl)adenosine
2-(6-Phenyl-1-hexynyl)adenosine
2-(Butenynyl)adenosine
2-(2-Cyclobutyl-1-ethynyl)adenosine
2-(2-Cyclopropyl-1-ethynyl)adenosine
2-(2-Cyclopentyl-1-ethynyl)adenosine (Compound 11)
2-(2-Cyclohexyl-1-ethynyl)adenosine (Compound 12)
2-(3-Cyclopropyl-1-propynyl)adenosine
2-(3-Cyclopentyl-1-propynyl)adenosine (Compound 13)
2-(3-Cyclohexyl-1-propynyl)adenosine (Compound 14)
2-(4-Cyclopropyl-1-butynyl) adenosine
2-(4-Cyclopentyl-1-butynyl)adenosine (Compound 15)
2-(4-Cyclohexyl-1-butynyl)adenosine
2-(5-Cyclopropyl-1-pentynyl)adenosine
(2) X=hydroxy-substituted hydrocarbon, Y=—$CH_2OH$
2-(3-Hydroxy-1-propynyl)adenosine (Compound 4)
2-(6-Hydroxy-1-hexynyl)adenosine
2-(3-Hydroxy-1-octynyl)adenosine
2-(3-Hydroxy-3-phenyl-1-propynyl)adenosine (Compound 5)
2-(3-Hydroxy-3-methyl-1-butynyl)adenosine
2-[2-(1-Hydroxycyclohexyl)-1-ethynyl]adenosine
2-[2-(1-Hydroxycyclopropyl)-1-ethynyl]adenosine
2-[3-(1-Hydroxycyclopropyl)-1-propynyl]adenosine
2-[4-(1-Hydroxycyclopropyl)-1-butynyl]adenosine
2-[5-(1-Hydroxycyclopropyl)-1-pentynyl]adenosine (3) X=azido-or cyano-substituted hydrocarbon, Y=—$CH_2OH$
2-(6-Azido-1-hexynyl)adenosine
2-(5-Cyano-1-pentynyl)adenosine
(4) X hydrocarbon oxy-substituted hydrocarbon, Y=—$CH_2OH$
2-(3-Methoxy-1-propynyl)adenosine
2-(3-Ethoxy-1-propynyl)adenosine (Compound 6)
2-(3-Butoxy-1-propynyl)adenosine
2-(4-Propoxy-1-butynyl)adenosine (Compound 7)
2-(4-Octoxy-1-butynyl)adenosine (Compound 8)
2-(5-Ethoxy-1-pentynyl)adenosine (Compound 9)
2-(3-Phenoxy-1-propynyl)adenosine
2-(3-Cyclohexyloxy-1-propynyl)adenosine (Compound 10)
(5) X=carboxy-substituted hydrocarbon, Y=—$CH_2OH$
2-(7-Carboxy-1-heptynyl)adenosine
2-(5-Carboxy-1-pentynyl)adenosine
2-(4-Ethoxycarbonyl-1-butynyl)adenosine
(6) X=(A)-substituted hydrocarbon, Y=—$CH_2OH$
2-(3-N-acetylamino-1-propynyl)adenosine
2-(3-N-benzoylamino-1-propynyl)adenosine
2-(3-N-trifluoroacetylamino-1-propynyl)adenosine
(7) X=(B)-substituted hydrocarbon, Y=—$CH_2OH$
2-(3-Phthalimidyl-1-propynyl)adenosine
2-(6-Phthalimidyl-1-hexynyl)adenosine (Compound 3)
2-[3-(3-Chlorophthalimidyl)-1-propynyl]adenosine
2-[3-(3-Methoxyphthalimidyl)-1-propynyl]adenosine
(8) X=(C)-substituted hydrocarbon, Y=—$CH_2OH$
2-(3-Dimethylamino-1-propynyl)adenosine
2-(6-Amino-1-hexynyl)adenosine
(9) X=acyl, Y=—$CH_2OH$
2-(3-Oxo-1-hexynyl)adenosine
2-(3-Oxo-1-heptynyl)adenosine
2-(3-Oxo-1-octynyl)adenosine
2-(3-Oxo-1-hexadecynyl)adenosine
(10) X=hydrocarbon, Y=substituted methyl
5'-Azido-5'-deoxy-2-(1-hexynyl)adenosine
5'-Amino-5'-deoxy-2-(1-hexynyl)adenosine
5'-Amino-5'-deoxy-2-(1-octynyl)adenosine
5'-Formylamino-5'-deoxy-2-(1-octynyl)adenosine
5'-Acetylamino-5'-deoxy-2-(1-hexynyl)adenosine
5'-(N'-methylureido)-5'-deoxy-2-(1-octynyl)adenosine
5'-(N'-methylthioureido)-5'-deoxy-2-(1-hexynyl)adenosine
5'-Methanesulfonylamino-5'-deoxy-2-(1-octynyl)adenosine
5'-p-Toluenesulfonylamino-5'-deoxy-2-(1-octynyl)adenosine
(11) X=hydrocarbon, Y=carbamoyl
2-(1-Octynyl)adenosine-4'-carboxamide
2-(1-Butynyl)adenosine-4'-methylcarboxamide
2-(1-Hexynyl)adenosine-4'-methylcarboxamide (Compound 16)
2-(1-Hexynyl)adenosine-4'-propylcarboxamide
2-(1-Octynyl)adenosine-4'-cyclopropylcarboxamide
(12) X=hydrocarbon, Y=carboxyl
2-(1-Octynyl)adenosine-4'-carboxylic acid
Methyl 2-(1-hexynyl)adenosine-4'-carboxylate
Ethyl 2-(1-hexynyl)adenosine-4'-carboxylate Of compounds belonging to the aforementioned groups (1) through (12), compounds belonging to groups (1), (2), (4), (7), and (11) are preferable. X is preferably an alkyl group which may be substituted by a group selected from among a cycloalkyl group, a hydroxycycloalkyl group, a phthalimido group, a hydroxy group, an alkoxy group, a cycloalkyloxy group, and an aryl group. Y is preferably a hydroxymethyl group or an alkyl-substituted carbamoyl group.

The 2-alkynyladenosine derivative, which is an active ingredient of the composition of the present invention, may assume a free form or an acid addition salt form. Examples of acid addition salts include inorganic acid salts such as hydrochlorides, sulfates, and hydrobromides; and organic acid salts such as oxalates, citrate, and malates.

Most 2-alkynyladenosine derivatives are known compounds, and all of the derivatives can be easily prepared through known processes (see Japanese Patent Application Laid-Open (kokai) Nos. 62-99330, 62-99395, 5-163294, 5-9197, 5-9198, and 5-25195; EP No. 429681; European Journal of Pharmacology, 196, 69–76 (1991); Journal of Medicinal Chemistry, 35 (2), 241–252 (1992); Journal of Medicinal Chemistry, 35 (12), 2253–2260 (1992); Journal of Medicinal Chemistry, 35 (15), 2881–2890 (1992); etc.)

As described below in Test Examples, the 2-alkynyladenosine derivative exhibits a remarkably excellent effect of lowering ocular tension as compared with the aforementioned CGS-21680, and the effect is long-lasting. Furthermore, the derivative exhibits high safety, and thus is useful as a remedy for eye diseases which require controlling of ocular tension to a low level, such as glaucoma. In addition, the 2-alkynyladenosine derivative exhibits the vasodilation effect and the effect of inhibiting platelet aggregation. Therefore, the derivative is expected to exhibit the effect of improving blood circulation at the optic papilla, which effect is considered important in the treatment of glaucoma.

The composition of the present invention may be prepared in a product form for oral administration or parenteral administration in accordance with the administration method. Examples of oral administration products include solid products such as powders, granules, capsules, and tablets. Examples of parenteral administration products include eye drops, eye ointments, and injections.

These products are produced through a customary process by adding pharmaceutically acceptable additives to the 2-alkynyladenosine derivative.

In the case of preparation of eye drops, if necessary, isotonization agents such as sodium chloride and glycerin; stabilizers such as sodium edetate; preservatives such as benzalkonium chloride and parabens; solution adjuvant such as polysorbate 80; or pH-regulating agents such as disodium hydrogenphosphate, sodium dihydrogenphosphate, boric acid, sodium tetraborate (borax), hydrochloric acid, and sodium hydroxide may be added to the 2-alkynyladenosine derivative, to thereby prepare eye drops through a customary process.

Eye ointments may be prepared by kneading the 2-alkynyladenosine derivative with, if necessary, eye ointment bases such as purified lanolin, petrolatum, liquid paraffin, and polyethylene glycol.

In the case of preparation of solid products for oral administration, the 2-alkynyladenosine derivative may be mixed with, if necessary, excipients such as lactose, starch, crystalline cellulose, calcium lactate, and calcium hydrogenphosphate; binders such as sucrose, hydroxypropyl cellulose, and polyvinylpyrrolidone; disintegrators such as carmellose calcium; or lubricants such as magnesium stearate and talc, to thereby produce a product through a customary process. These solid products may be coated with enteric bases such as hydroxypropylmethyl cellulose phthalate and a methacrylic acid-methyl methacrylate copolymer, to thereby produce enteric drugs.

In the case of preparation of injections, the 2-alkynyladenosine derivative is dissolved in injection water, if necessary, together with pH-regulating agents such as hydrochloric acid, sodium hydroxide, disodium hydrogenphosphate, and sodium dihydrogenphosphate; or isotonization agents such as sodium chloride. The resultant solution is subjected to sterile filtration, and then placed in ampoules. In addition, the solution may be mixed with mannitol or gelatin and then freeze-dried under vacuum, in which case the resultant product is prepared into an injection upon use.

The dose of the 2-alkynyladenosine derivative, which is an active ingredient of the composition of the present invention, is appropriately determined in accordance with the age, weight, and pathological conditions of the patient, and the product form of the composition Eye drops or eye ointments containing the derivative in an amount of 0.0001–10% (w/v) are preferably instilled or applied several times per day. In the case of oral administration agents or injections, the daily dose of the derivative is usually 0.001–1,000 mg for an adult, and the daily dose is preferably administered in a single dose, or in divided doses several times a day.

EXAMPLES

The present invention will next be described in more detail by way of Examples, which should not be construed as limiting the invention thereto.

Formulation Example 1 Eye Drop Solution

| | |
|---|---|
| 2-(1-Octynyl)adenosine (Compound 2) | 0.1 g |
| Sodium dihydrogenphosphate (dodecahydrate) | 1.41 g |
| Disodium hydrogenphosphate (dihydrate) | 0.37 g |
| Sodium chloride | 0.26 g |
| Polysorbate 80 | 0.5 g |
| Benzalkonium chloride | 5 mg |
| Sterilized water | appropriate amount |
| | Total 100 mL |

According to the above formulation, an eye drop solution was prepared, and the resultant eye drop solution was placed in polypropylene-made eye drop containers (5 mL for each container).

Formulation Example 2 Eye Ointment

| | |
|---|---|
| 2-(1-Octynyl)adenosine (Compound 2) | 0.5 g |
| Liquid paraffin | 1.0 g |
| White petrolatum | appropriate amount |
| | Total 100 g |

The above ingredients were kneaded, to thereby prepare an eye ointment, and the resultant eye ointment was placed in aluminum-made eye drop tubes (3 g per tube).

Formulation Example 3 Oral Administration Agent

| | |
|---|---|
| 2-(1-Octynyl)adenosine (Compound 2) | 25 mg |
| Potato starch | 15 mg |
| Crystalline cellulose | 20 mg |
| Hydroxypropyl cellulose | 5 mg |
| Magnesium stearate | 2 mg |
| Lactose | appropriate amount |
| | Total 150 mg (per tablet) |

According to the above formulation, 2-(1-octynyl) adenosine, potato starch, crystalline cellulose, hydroxypropyl cellulose, and lactose were mixed, and water was added to the resultant mixture. Subsequently, the mixture was kneaded, and then granulated through pressing with a screen. After the resultant granules were dried, magnesium stearate was added to the dried granules, to thereby produce tablets.

Formulation Example 4 Injection

| | |
|---|---|
| 2-(1-Octynyl)adenosine (Compound 2) | 0.25 g |
| Polysorbate 80 | 5 g |
| Sodium chloride | 8 g |
| Injection water | appropriate amount |
| | Total 1000 mL |

According to the above formulation, an injection was prepared. The resultant injection was subjected to sterile filtration, and then placed in glass ampoules (2 mL per ampoule).

Synthesis Examples (1) Compound 5: 2-(3-Hydroxy-3-phenyl-1-propynyl) adenosine

2-Iodoadenosine and 1-phenyl-2-propyn-1-ol were subjected to known cross-coupling reaction (J. Med. Chem. 35, 241–252 (1992)) in the presence of a palladium catalyst, to thereby synthesize a crude product. The product was purified with silica gel, to thereby yield 2-(3-hydroxy-3-phenyl-1-propynyl)adenosine.

$^1$H-NMR (DMSO-$d_6$, ppm): 8.43 (1H, s), 7.55–7.32 (7H, m), 6.27 (1H, d, J=5.9 Hz), 5.86 (1H, d, J=5.9 Hz), 5.60 (1H, d, J=5.9 Hz), 5.47 (1H, d, J=4.9 Hz), 5.18–5.15 (2H, m), 4.50 (1H, q, J=4.9 Hz), 4.14–4.11 (1H, m), 3.96–3.93 (1H, m), 3.70–3.53 (2H, m).

(2) Compound 6: 2-(3-Ethoxy-1-propynyl)adenosine

Propargyl alcohol was dissolved in DMF, and 60% sodium hydride was added to the resultant solution. The mixture was stirred for one hour for reaction at room temperature. After completion of reaction, ethyl bromide was added to the reaction mixture, and the mixture was allowed to react at room temperature overnight, to thereby yield 3-ethoxypropyne.

To the reaction mixture containing 3-ethoxypropyne, 6-chloro-2',3',5'-triacetyl-2-iodopurine riboside was added, and the mixture was subjected to known cross-coupling reaction in the presence of a palladium catalyst and to amination and deacylation in the presence of concentrated ammonia (EP No. 429681), to thereby synthesize a crude product. The product was purified with silica gel, to thereby yield 2-(3-ethoxy-1-propynyl)adenosine. mp: 120–127° C.

(3) Compound 10: 2-(3-Cyclohexyloxy-1-propynyl) adenosine

Cyclohexanol was dissolved in THF, and 60% sodium hydride was added to the resultant solution. The mixture was stirred for one hour for reaction at room temperature. After completion of reaction, DMF and propargyl bromide were added to the reaction mixture, and the mixture was allowed to react at room temperature for one hour and then at 80° C. for two hours, to thereby yield 3-cyclohexyloxypropyne.

To the reaction mixture containing 3-cyclohexyloxypropyne, 6-chloro-2',3',5'-triacetyl-2-iodopurine riboside was added, and the mixture was subjected to known cross-coupling reaction in the presence of a palladium catalyst and to amination and deacylation reaction in the presence of concentrated ammonia (EP No. 429681), to thereby synthesize a crude product. The product was purified with silica gel, to thereby yield 2-(3-cyclohexyloxy-1-propynyl)adenosine.

$^1$H-NMR (DMSO-$d_6$, ppm): 8.42 (1H, m), 7.47 (2H, s), 5.85 (1H, d, J=5.9 Hz), 5.45 (1H, d, J=5.9 Hz), 5.19–5.16 (2H, m), 4.56–4.52 (1H, m), 4.38 (2H, s), 4.15–4.11 (1H, m), 3.97–3.94 (1H, m), 3.69–3.35 (3H, m), 1.90–1.18 (9H, m).

Test Example 1

(Test Methods)

2-(1-Octynyl)adenosine, 2-(3-hydroxy-1-propynyl) adenosine, and CGS-21680 [2-((4-(2-carboxyethyl) phenylethyl)amino)adenosine-5'-N-ethyluronamide] were used as test compounds. Each compound was dissolved in a 15% aqueous solution of dimethyl sulfoxide (hereinafter the solution will be referred to as an "eye drop base"), to thereby obtain a test solution. The amounts of 2-(1-octynyl) adenosine and 2-(3-hydroxy-1-propynyl)adenosine were 0.03% (W/V) and 0.1% (W/V), respectively. The amount of CGS-21680 in the resultant solution was 0.1% (w/v). The eye drop base was employed as a control.

New Zealand white male rabbits (Tokyo Jikken Dobutsu) (weight: 2.2–3.1 kg) were employed in the test. The rabbits were retained in a box-type fixation apparatus and employed in the test.

The ocular tension of each rabbit was measured by use of an applanation pneumatonometer (Alcon, PTG) without anesthesia. Before the ocular tension was measured, 0.4% oxybuprocaine hydrochloride (Benoxil 0.4% eye drop, product of Santen Pharmaceutical Co., Ltd.) was instilled to the eyes of each rabbit, to thereby anesthetize the surface of the cornea. Before administration of drugs, the ocular tension of each rabbit was measured several times at 15-minute intervals until the ocular tension became stable. After the ocular tension became stable, the ocular tension was measured three times, and the average value was employed as the normal ocular tension.

Subsequently, each of the test solutions (50 μL) was instilled once to either the left or right eye of the each of the respective rabbits. The ocular tension was measured 15, 30, 45, 60, 90, 120, 150, and 180 minutes after instillation of the test compound. Simultaneously, the ocular tension of the remaining eye to which the test solution was not instilled was measured. Six rabbits were employed for each test compound. For control, the eye drop base was instilled to the eye of the rabbit, and the ocular tension was measured in a manner similar to that described above.

The test results are shown by average value±standard error. Significance testing was carried out by means of multiple comparison according to the Dunnett test.

(Test Results)

Figure 2:
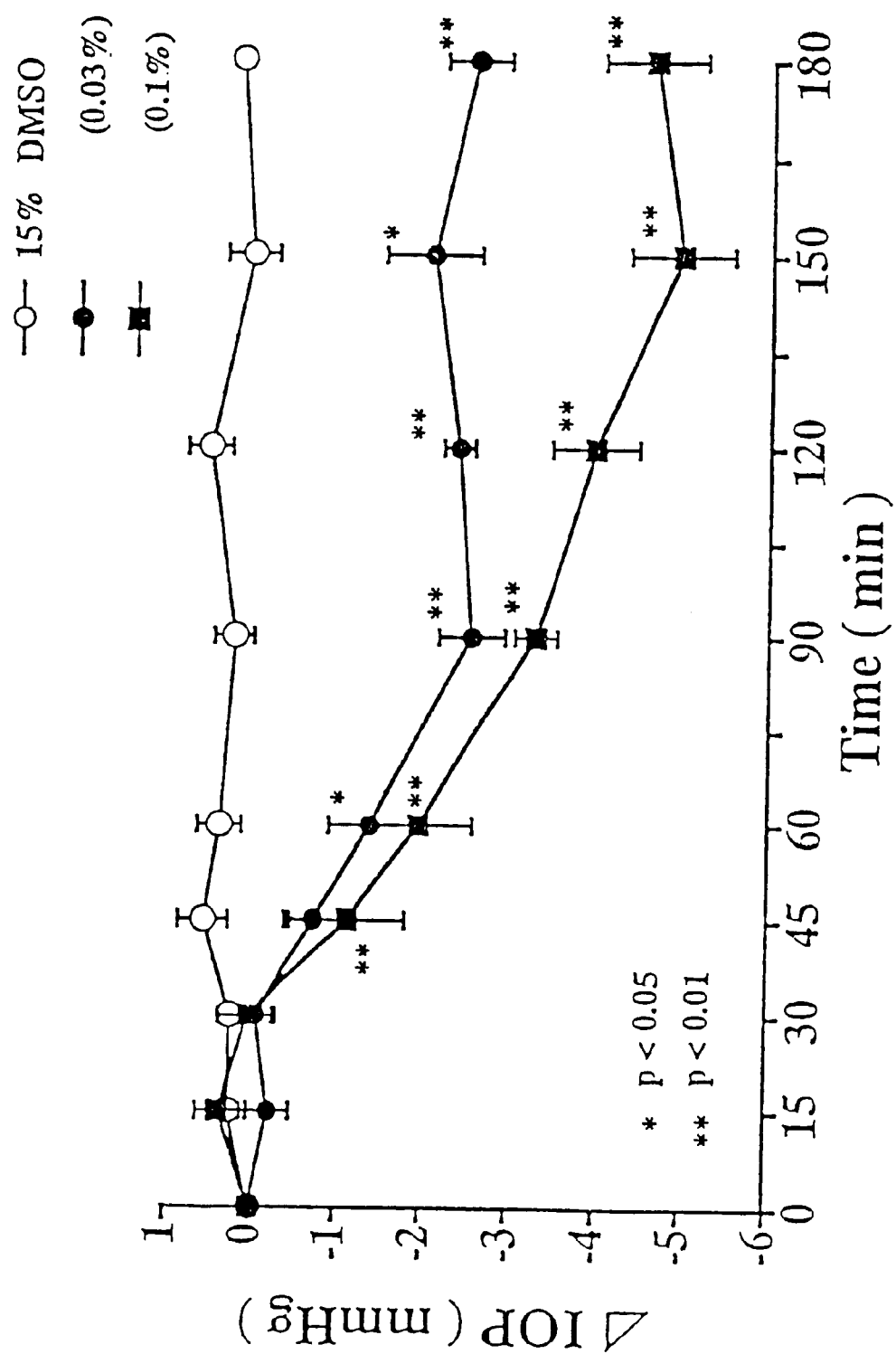
FIG. 2 shows the effect of 2-(2-hydroxy-1-propynyl) adenosine (●, ■) against ocular tension in rabbits when administered to the rabbits. The y axis represents change in ocular tension (ΔIOP), and the x axis represents time (minutes) elapsed after administration.

The results are shown in FIGS. 1 and 2. When the eye drop base is instilled, the ocular tension of the rabbit does not vary to any significant extent, whereas when the respective test compounds are instilled, the normal ocular tension of the rabbit lowers dose-dependently. As is apparent from the figures, 2-(1-octynyl)adenosine and 2-(3-hydroxy-1-propynyl)adenosine exhibit excellent effect of lowering ocular tension, as compared with CGS-21680. In addition, the compounds exhibit long-lasting effect of lowering ocular tension.

Test Example 2

(Test Methods)

Compounds shown in Table 1 were used as test compounds. Each compound was dissolved in saline containing polysorbate 80 (hereinafter the saline will be referred to as "eye drop base A") or in an aqueous solution of boric acid buffer (pH 7.0) containing polysorbate 80 (hereinafter the solution will be referred to as "eye drop base B") (polysorbate 80 content of each base: 5 mg/mL), to thereby obtain a test solution. The amount of each compound in the resultant solution was 0.1% (W/V). The eye drop bases were employed as a control.

Japanese white male rabbits (Kitayama Labes Co., Ltd.) (weight: 2.1–3.2 kg) were employed in the test. The rabbits were retained in a box-type fixation apparatus and employed in the test.

The ocular tension of each rabbit was measured by use of Model 30 Classic Pneumatonometer (product of Mentor) without anesthesia. Before the ocular tension was measured, 0.4% oxybuprocaine hydrochloride (Benoxil 0.4% eye drop solution, product of Santen Pharmaceutical Co., Ltd.) was instilled to the eyes of each rabbit, to thereby anesthetize the surface of the cornea. The ocular tension of each rabbit was measured several times at regular intervals. After the ocular tension became stable, the ocular tension was measured three times, and the average value was employed as the ocular tension.

A 0.1% solution of each test compound (50 μL) was instilled to one eye of each of the respective rabbits, and simultaneously the eye drop base (50 μL) was instilled to the remaining eye. The ocular tensions of both eyes were measured 60 minutes before instillation of the test compound; 0 minute immediately before instillation; and 30, 60, 90, 120, 150, 180, 240, 300, 360, 420, and 480 minutes after instillation. Two to six rabbits were employed for each test compound. For control, the eye drop base was instilled to both eyes of each respective rabbit, and the ocular tension was measured in a manner similar to that described above.

For each test compound, the effect of lowering ocular tension was evaluated on the basis of the following values: the area under the curve of time versus change in difference between the ocular tension of the eye to which the test compound was instilled and that of the eye to which the eye drop base was instilled (hereinafter the area will be abbreviated as AUC (mmHg·min)); and the maximum value of difference between the ocular tension of the eye to which the test compound was instilled and that of the eye to which the eye drop base was instilled (hereinafter the value will be abbreviated as Emax (mmHg)).

(Test Results)

The AUC and Emax of each respective test compound are shown in Table 1. The results reveal that instillation of the respective test compounds (0.1%) lowers the ocular tension of the rabbit with respect to the normal ocular tension thereof, and that the effect of lowering ocular tension is long lasting. In contrast, when the eye drop base is instilled, the ocular tension of the rabbit does not vary to any significant extent. As is apparent from the results, the compounds exhibit remarkable long-lasting effect of lowering ocular tension.

TABLE 1

Effect of lowering ocular tension after instillation of test compound to rabbit of normal ocular tension

| Test compound | AUC (mmHg.min) | Emax (mmHg) | Eye drop base |
| --- | --- | --- | --- |
| Compound 1 | −1236.0 | −4.6 | B |
| Compound 2 | −1093.5 | −4.2 | A |
| Compound 3 | −1471.0 | −6.3 | A |
| Compound 4 | −955.6 | −4.3 | A |
| Compound 5 | −1185.6 | −4.8 | A |
| Compound 6 | −1538.3 | −5.3 | A |
| Compound 7 | −1828.5 | −4.9 | B |

TABLE 1-continued

Effect of lowering ocular tension after instillation of test compound to rabbit of normal ocular tension

| Test compound | AUC (mmHg.min) | Emax (mmHg) | Eye drop base |
| --- | --- | --- | --- |
| Compound 8 | −1683.0 | −5.4 | B |
| Compound 9 | −1117.5 | −3.7 | B |
| Compound 10 | −945.9 | −4.3 | A |
| Compound 11 | −1532.7 | −4.4 | B |
| Compound 12 | −1670.2 | −6.0 | B |
| Compound 13 | −1053.9 | −5.9 | B* |
| Compound 14 | −1053.2 | −4.0 | B |
| Compound 15 | −1086.0 | −5.6 | B |
| Compound 16 | −1838.3 | −6.0 | A |
| CGS-21680 | −508.1 | −2.5 | A |
| Eye drop base A | −30.4 | −0.4 | |
| Eye drop base B | −31.5 | −0.2 | | n = 6 (*n = 2)

Compound 1: 2-(1-hexynyl)adenosine
Compound 2: 2-(1-octynyl)adenosine
Compound 3: 2-(6-phthalimidyl-1-hexynyl)adenosine
Compound 4: 2-(3-hydroxy-1-propynyl)adenosine
Compound 5: 2-(3-hydroxy-3-phenyl-1-propynyl)adenosine
Compound 6: 2-(3-ethoxy-1-propynyl)adenosine
Compound 7: 2-(4-propoxy-1-butynyl)adenosine
Compound 8: 2-(4-octoxy-1-butynyl)adenosine
Compound 9: 2-(5-ethoxy-1-pentynyl)adenosine
Compound 10: 2-(3-cyclohexyloxy-1-propynyl)adenosine
Compound 11: 2-(2-cyclopentyl-1-ethynyl)adenosine
Compound 12: 2-(2-cyclohexyl-1-ethynyl)adenosine
Compound 13: 2-(3-cyclopentyl-1-propynyl)adenosine
Compound 14: 2-(3-cyclohexyl-1-propynyl)adenosine
Compound 15: 2-(4-cyclopentyl-1-butynyl)adenosine
Compound 16: 2-(1-hexynyl)adenosine-4'-methylcarboxamide Test Example 3

Test Methods

To six-week-old male and female SD rats (six for each group), 2-(1-octynyl)adenosine was administered orally at a single dose of 521, 729, 1020, 1429, or 2000 mg/kg. The resultant rats and control group rats to which a solvent was administered were observed for two weeks.

To nine-month-old male and female beagle dogs (two for each group), 2-(1-octynyl)adenosine was administered orally at a single dose of 50, 150, or 450 mg/kg. The resultant dogs and control group dogs to which a empty capsule was administered were observed for two weeks.

Test Results

The $LD_{50}$ values of 2-(1-octynyl)adenosine against the rat and the dog are presumed to be 2000 mg/kg or more and 450 mg/kg or more, respectively, which are maximum doses.

Industrial Applicability

The composition of the present invention exhibits long-lasting and excellent effect of lowering ocular tension, and the composition is useful as a medicinal composition for treating eye diseases such as glaucoma and hypertonia oculi.

What is claimed is:

1. A method for lowering ocular tension, comprising:

administering to a subject in need thereof an effective amount of a compound of formula (1):

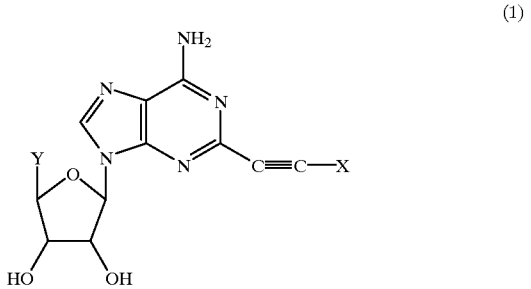

in free form or in pharmaceutically acceptable acid addition salt form, wherein X represents a $C_4$ to $C_6$ hydrocarbon; a $C_4$ hydrocarbon substituted with phthalimidyl; or a $C_1$ to $C_6$ hydrocarbon substituted with hydroxy, hydroxyphenyl, a $C_2$ to $C_8$ alkoxy, a $C_6$ cycloalkoxy, or a $C_5$ to $C_6$ cycloalkyl, and Y represents a hydroxy substituted methyl or hydroxy substituted methyl carboxamide.

2. The method of claim 1, wherein the compound of formula (1) is selected from the group consisting of:

2-(1-hexynyl)adenosine,
2-(1-octynyl)adenosine,
2-(6-phthalimidyl-1-hexynyl)adenosine,
2-(3-hydroxy-1-propynyl)adenosine,
2-(3-hydroxy-3-phenyl-1-propynyl)adenosine,
2-(3-ethoxy-1-propynyl)adenosine,
2-(4-propoxy-1-butynyl)adenosine,
2-(4-octoxy-1-butynyl)adenosine,
2-(5-ethoxy-1-pentynyl)adenosine,
2-(3-cyclohexyloxy-1-propynyl)adenosine,
2-(2-cyclopentyl-1-ethynyl)adenosine,
2-(2-cyclohexyl-1-ethynyl)adenosine,
2-(3-cyclopentyl-1-propynyl)adenosine,
2-(3-cyclohexyl-1-propynyl)adenosine,
2-(4-cyclopentyl-1-butynyl)adenosine, and
2-(1-hexynyl) adenosine-4'-methylcarboxamide.

3. The method of claim 1, wherein X represents a $C_4$ to $C_6$ hydrocarbon.

4. The method of claim 1, wherein X represents a $C_1$ to $C_6$ hydrocarbon substituted with hydroxy, hydroxyphenyl, a $C_2$ to $C_8$ alkoxy, a $C_6$ cycloalkoxy, or a $C_5$ to $C_6$ cycloakyl.

5. The method of claim 1, wherein Y represents a hydroxy substituted methyl.

6. The method of claim 1, wherein Y represents a hydroxy substituted methyl carboxamide.

7. A method for treating glaucoma, comprising:

administering to a subject in need thereof an effective amount of a compound of formula (1):

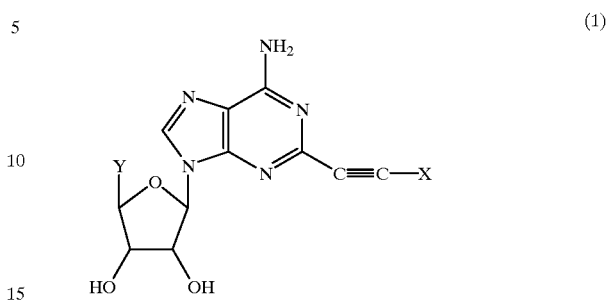

in free form or in pharmaceutically acceptable acid addition salt form, wherein X represents a $C_4$ to $C_6$ hydrocarbon, a $C_4$ hydrocarbon substituted with phthalimidyl; a $C_1$, to $C_6$ hydrocarbon substituted with hydroxy, hydroxyphenyl, a $C_2$ to $C_8$ alkoxy, a $C_6$ cycloalkoxy, or a $C_5$ to $C_6$ cycloalkyl, and Y represents a hydroxy substituted methyl or hydroxy substituted methyl carboxamide.

8. The method of claim 7, wherein X represents a $C_4$ to $C_6$ hydrocarbon.

9. The method of claim 7, wherein X represents a $C_1$ to $C_6$ hydrocarbon substituted with hydroxy, hydroxyphenyl, a $C_2$ to $C_8$ alkoxy, a $C_6$ cycloalkoxy, or a $C_5$ to $C_6$ cycloalkyl.

10. The method of claim 7, wherein Y represents a hydroxy substituted methyl.

11. The method of claim 7, wherein Y represents a hydroxy substituted methyl carboxamido.

12. The method of claim 7, wherein the compound of formula (1) is selected from the group consisting of:

2-(1-hexynyl)adenosine,
2-(1-octynyl)adenosine,
2-(6-phthalimidyl-1-hexynyl)adenosine,
2-(3-hydroxy-1-propynyl)adenosine,
2-(3-hydroxy-3-phenyl-1-propynyl)adenosine,
2-(3-ethoxy-1-propynyl)adenosine,
2-(4-propoxy-1-butnyl)adenosine,
2-(4-octoxy-1-butynyl)adenosine,
2-(5-ethoxy-1-pentynyl)adenosine,
2-(3-cyclohexyloxy-1-propynyl)adenosine,
2-(2-cyclopentyl-1-ethynyl)adenosine,
2-(2-cyclohexyl-1-ethynyl)adenosine,
2-(3-cyclopentyl-1-propynyl)adenosine,
2-(3-cyclohexyl-1-propynyl)adenosine,
2-(4-cyclopentyl-1-butynyl)adenosine, and
2-(1-hexynyl)adenosine-4'-methylcarboxamide.

13. A method for treating ocular hypertonia, comprising:

administering to a subject in need thereof an effective amount of a compound of formula (1):

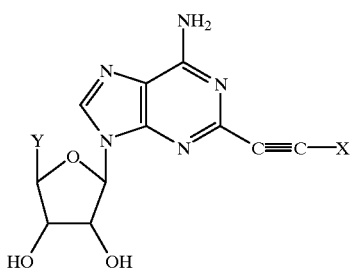

in free form or in pharmaceutically acceptable acid addition salt form, wherein X represents a $C_4$ to $C_6$ hydrobon, a $C_4$ hydrocarbon substituted with phthalimidyl; a $C_1$ to $C_6$ hydrocarbon substituted with hydroxy, hydroxyphenyl, a $C_2$ to $C_8$ alkoxy, a $C_6$ cycloalkoxy, or a $C_5$ to $C_6$ cycloalkyl, and Y represents a hydroxy substituted methyl or hydroxy substituted methyl carboxamide.

14. The method of claim 13, wherein X represents a $C_4$ to $C_6$ hydrocarbon.

15. The method of claim 13, wherein X represents a $C_1$ to $C_6$ hydrocarbon substituted with hydroxy, hydroxyphenyl, a $C_2$ to $C_8$ alkoxy, a $C_6$ cycloalkoxy, or a $C_5$ to $C_6$ cycloalkyl.

16. The method of claim 13, wherein Y represents a hydroxy substituted methyl.

17. The method of claim 13, wherein Y represents a hydroxy substituted methyl carboxamide.

18. The method of claim 13, wherein the compound of formula (1) is selected from the group consisting of:
2-(1-hexynyl)adenosine,
2-(1-octynyl)adenosine,
2-(6-phthalimidyl-1-hexynyl)adenosine,
2-(3-hydroxy-1-propynyl)adenosine,
2-(3-hydroxy-3-phenyl-1-propynyl)adenosine,
2-(3-ethoxy-1-propynyl)adenosine,
2-(4-propoxy-1-butynyl)adenosine,
2-(4-octoxy-1-butynyl)adenosine,
2-(5-ethoxy-1-pentynyl)adenosine,
2-(3-cyclohexyloxy-1-propynyl)adenosine,
2-(2-cyolopentyl-1-ethynyl)adenosine,
2-(2-cyclohexyl-1-ethynyl)adenosine,
2-(3-cyclopentyl-1-propynyl)adenosine,
2-(3-cyclohexyl-1-propynyl)adenosine,
2-(4-cyclopentyl-1-butynyl)adenosine, and
2-(1-hexynyl)adenosine-4'-methylcarboxamide.

* * * * *